Figure 1:
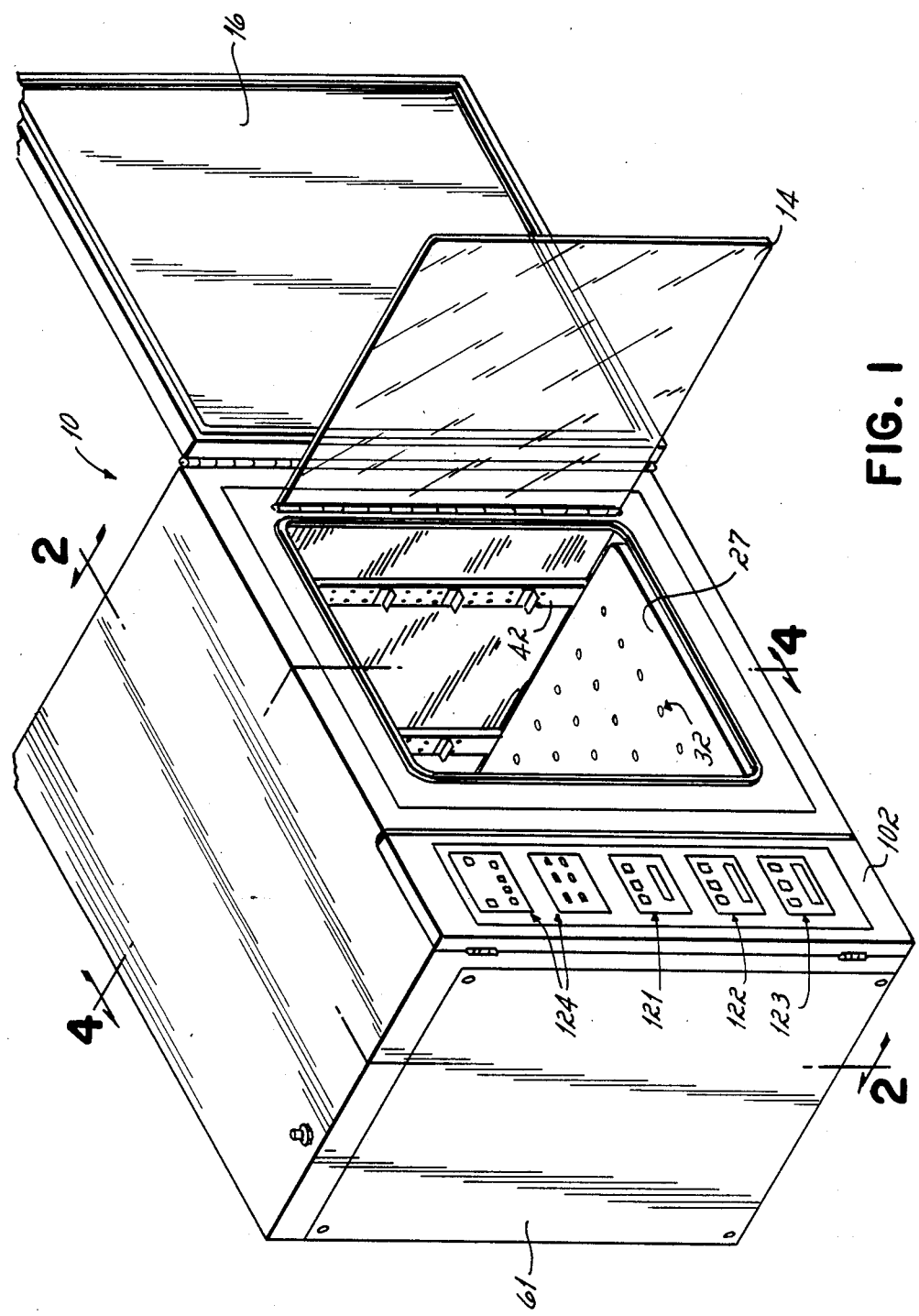

United States Patent [19]

Selfridge et al.

[11] Patent Number: 4,572,427

[45] Date of Patent: Feb. 25, 1986

[54] CONTROLLED ATMOSPHERE ENCLOSURE

[75] Inventors: Glenn D. Selfridge, Marietta, Ohio; Russell C. Tipton, Williamstown, W. Va.

[73] Assignee: Mallinckrodt, Inc., Hazelwood, Mo.

[21] Appl. No.: 585,854

[22] Filed: Mar. 2, 1984

[51] Int. Cl.$^4$ .............................................. A01G 23/10
[52] U.S. Cl. .................... 236/3; 236/44 C; 236/91 C; 165/146; 219/407
[58] Field of Search ............ 237/14, 15; 236/3, 44 C, 236/19 C; 165/72, 73, 75, 146; 219/391, 398, 397, 406, 407, 408

[56] References Cited

U.S. PATENT DOCUMENTS

| | | | |
|---|---|---|---|
| 615,669 | 12/1898 | Beers | 236/3 |
| 2,470,046 | 5/1949 | Napier | 236/3 |
| 3,553,426 | 1/1971 | Fink | 236/3 |
| 4,298,789 | 11/1981 | Eichelbergel et al. | 219/391 |

Primary Examiner—Henry Bennett
Attorney, Agent, or Firm—Wood, Herron & Evans

[57] ABSTRACT

An incubator for laboratory use which includes a housing defining a thermally insulated inner chamber having a controlled gas atmosphere. Devices for sensing characteristics of the incubator chamber atmosphere, and for conditioning the atmosphere, are positioned in a gas recirculation path outside the incubator chamber. The gas atmosphere of the incubator chamber circulates from a chamber outlet in an upper portion of the chamber, through the recirculation path, returning to the incubator chamber through a chamber inlet in a lower portion of the chamber. Included in the recirculation path are a blower for recirculating the chamber atmosphere, a filter, a $CO_2$ sensor, and a humidifier. A microprocessor-based controller is responsive to the output of the $CO_2$ sensor to effect the addition of $CO_2$ to the recirculating gas to maintain a selected $CO_2$ level in the chamber atmosphere. Upper and lower diffuser plates in the incubator chamber define upper and lower plenums, respectively. The upper plenum communicates with the chamber outlet, and the lower plenum communicates with the chamber inlet, to produce an upward vertical laminar flow of the gas atmosphere through the chamber. The incubator chamber walls are spaced inwardly from insulated outer walls to provide an enclosed air space about the outside of the chamber wall. Heaters inside the air space, spaced apart from the inner wall, are sized to produce substantially even heating of the chamber through convection in the air space.

4 Claims, 15 Drawing Figures

CONTROLLED ATMOSPHERE ENCLOSURE

DESCRIPTION OF THE INVENTION

This invention relates generally to controlled gas atmosphere enclosures and more particularly concerns such enclosures for laboratory use, such as the growth of biological cultures. The invention is disclosed particularly in relation to a thermally insulated and heated enclosure employed as an incubator.

There are a number of commercial applications for controlled gas atmosphere enclosures. For example, electrical components and circuits are often tested in enclosures at a selected temperature and/or relative humidity for a period of time. Another common application for controlled atmosphere enclosures is the growth of biological cultures in the laboratory. As will be discussed herein with regard to a particular embodiment, the present invention may be advantageously employed in connection with a controlled gas atmosphere incubator in which a chamber for biological cultures is heated and in which the atmosphere of the chamber is controlled as to one or more constituent gases and/or the relative humidity.

A typical incubator of the foregoing type includes a generally cubical outer housing made up of five insulated walls (top, bottom, left side, right side, and rear) and an insulated front door. The door is mounted on hinges on the front of one of the side walls and may be opened to permit access to the interior of the incubator. When the door is closed, it is suitably sealed about its periphery to the housing walls to form the sixth wall of the housing. The incubator chamber, in which biological cultures are grown, is formed by inner walls, inside the insulated outer walls, and typically includes shelves upon which culture containers are placed. The shelves are carried by suitable shelf supports inside the chamber.

Most incubators of this type are either water jacket incubators or forced draft incubators. In a water jacket incubator the inner chamber is heated to the desired temperature by a sealed jacket of water surrounding the five fixed sides of the incubator chamber. The water jacket lies between the chamber wall and the insulated housing walls and is heated by heating elements in thermal contact with the water in the water jacket. Due to the thermal conductivity of water, the heat from the individual heating elements is relatively evenly dispersed over the water in the water jacket, providing even heating of the chamber. Such even heating is desirable in order to provide a uniform temperature for the biological cultures in different areas within the chamber and in order to prevent "cold spots" on the inner chamber wall upon which condensation can form.

Although the heating of the chamber walls in a water jacket incubator is substantially uniform, the chamber atmosphere will stratify thermally if the chamber atmosphere is undisturbed. When such stratification occurs, the temperature of the chamber atmosphere is greater at the top of the chamber than at the bottom of the chamber. In addition, if a constituent gas concentration is maintained in the chamber, such as a particular $CO_2$ level, the constituent gas will also stratify within the chamber atmosphere. Consequently, it is desirable to maintain a certain rate of flow within the chamber to assure uniformity of temperature and of constituent gases. In order to do this, typically a portion of the chamber is separated from the main chamber area by a wall to define a duct extending, for example, along a side of the chamber. A small blower or fan is placed in the duct and the chamber atmosphere is circulated, such as from a duct inlet in the upper portion of the chamber to a duct outlet in a lower portion of the chamber.

In a forced draft incubator, the inner chamber walls are insulated from the outer housing walls by a layer of insulation inside the housing walls. However, in this case there is no water jacket interposed between the insulated outer walls and the inner chamber walls. To obtain heating of the chamber in a forced draft incubator, some type of duct, such as described above, is typically provided within the chamber, and a fan and a heating element are mounted in the duct. As the fan circulates air from the main chamber area through the duct, the circulated chamber atmosphere is heated by the heating element. In order to heat the chamber atmosphere substantially uniformly, and to the desired temperature, considerably greater air flow is required than in the case of a water jacket incubator.

In a typical forced draft incubator, or water jacket incubator, if a constituent gas in the atmosphere of the incubator chamber is to be maintained at a particular level, a probe is introduced into the chamber, perhaps within the duct through which the chamber atmosphere circulates. In the case of $CO_2$, for example, a $CO_2$ sensor is introduced into the incubator chamber to measure the concentration of $CO_2$ therein. A source of $CO_2$ is then coupled to the interior of the chamber through a controlled valve, with an automatic control system actuating the valve as required to maintain the $CO_2$ concentration in the chamber at a selected level.

The humidity in a forced draft incubator is also often controlled. Rather than introducing steam or water into the incubator chamber as may be done in the case of a water jacket incubator, in a forced draft incubator quite often a pan of water is placed upon the floor of the incubator chamber, and the recirculated chamber atmosphere is directed out of the bottom of a duct across the surface of the water in the pan. Due to the higher recirculation rates in a forced draft incubator, appropriate humidification of the chamber is obtained.

In either a forced draft or a water jacket incubator, sensors such as for $CO_2$ or humidity have typically been located within the chamber atmosphere itself, although perhaps within a recirculation duct, as earlier described. Such sensors in the chamber are subject to the chamber atmosphere, and a sensor can fail or suffer performance degradations due to contaminants or the accumulation of a coating on the sensor. The presence of such sensors in the incubator chamber itself also makes cleaning of the chamber interior more difficult. In fact, the very existence of a duct or the like for the circulation of the chamber atmosphere within the chamber introduces difficulties in cleaning the chamber.

The recirculation of the chamber atmosphere, such as through a duct, in either type of incubator presents yet another problem, that of potential contamination of biological cultures within the chamber. Contaminants such as mold spores are almost invariably present in the chamber atmosphere and may be directed by the recirculatory air flow into the biological culture containers such as 96 well plates. Culture contamination problems are exacerbated by the higher air flows required in forced draft incubators.

Higher air flow rates involved in forced draft incubators have a further disadvantage in that the higher flow rates tend to dry out biological culture media. To a large degree, the necessity of offsetting this desiccation results in the requirement for humidity control in forced draft incubators. In such incubators, a relatively high humidity is maintained so that the drying effect of the gas flow is ameliorated.

Despite the advantages of a water jacket incubator with regard to reduced desiccation and culture contamination, such incubators have the disadvantage of the increased cost of providing a water-tight jacket to surround the incubator chamber. The larger the size of the incubator chamber, the greater the expense and difficulty in providing the requisite water jacket.

There are a number of objectives to be met by the incubator which is presently disclosed. The present incubator overcomes the above-discussed problems of sensor contamination and further avoids the difficulties of desiccation of biological cultures and their contamination by rapid rates of flow of the atmosphere in the incubator chamber. These desirable results are obtained without the employment of a water jacket for heating the incubator chamber.

The foregoing objectives have been accomplished in the presently disclosed incubator in a number of ways. The present incubator, for example, employs a warm air jacket heating system for the incubator chamber which eliminates the requirement for a water-tight jacket surrounding the incubator chamber. Uniform heating of the chamber by the air jacket is provided by scaling the heating capacity of heating elements, located in an air space surrounding the incubator chamber, so that even heating is obtained by convection within the air space.

In the presently disclosed incubator, there are no sensors or fans in the incubator chamber, thereby eliminating the problems of sensor contamination and difficulties in cleaning the interior of the chamber. Instead, a recirculation path totally outside the chamber is provided, with a filter in the recirculation path to substantially eliminate contamination of sensors downstream from the filter. In the disclosed form of incubator, $CO_2$ sensing, and the addition of $CO_2$ as required, are accomplished in the recirculation path. In addition, humidification of the chamber atmosphere is accomplished by the provision of a humidifier outside the chamber in the recirculation path.

Desiccation of cultures is substantially reduced from that which can occur with forced draft incubators since the requisite recirculation rate for the chamber atmosphere is on the same order as that required for a water jacket incubator. Further, culture contamination problems are avoided by the provision of diffusers in the upper and lower portions of the incubator chamber. The lower diffuser defines a plenum in the bottom of the incubator chamber, communicating with a chamber inlet from the recirculation path, and the upper diffuser defines a plenum which communicates with a chamber outlet to the recirculation path. The diffusers, in the form of incubator to be described, comprise apertured diffuser plates, which cooperate to provide a laminar upward vertical flow of the gas atmosphere within the incubator chamber.

Figure 2:
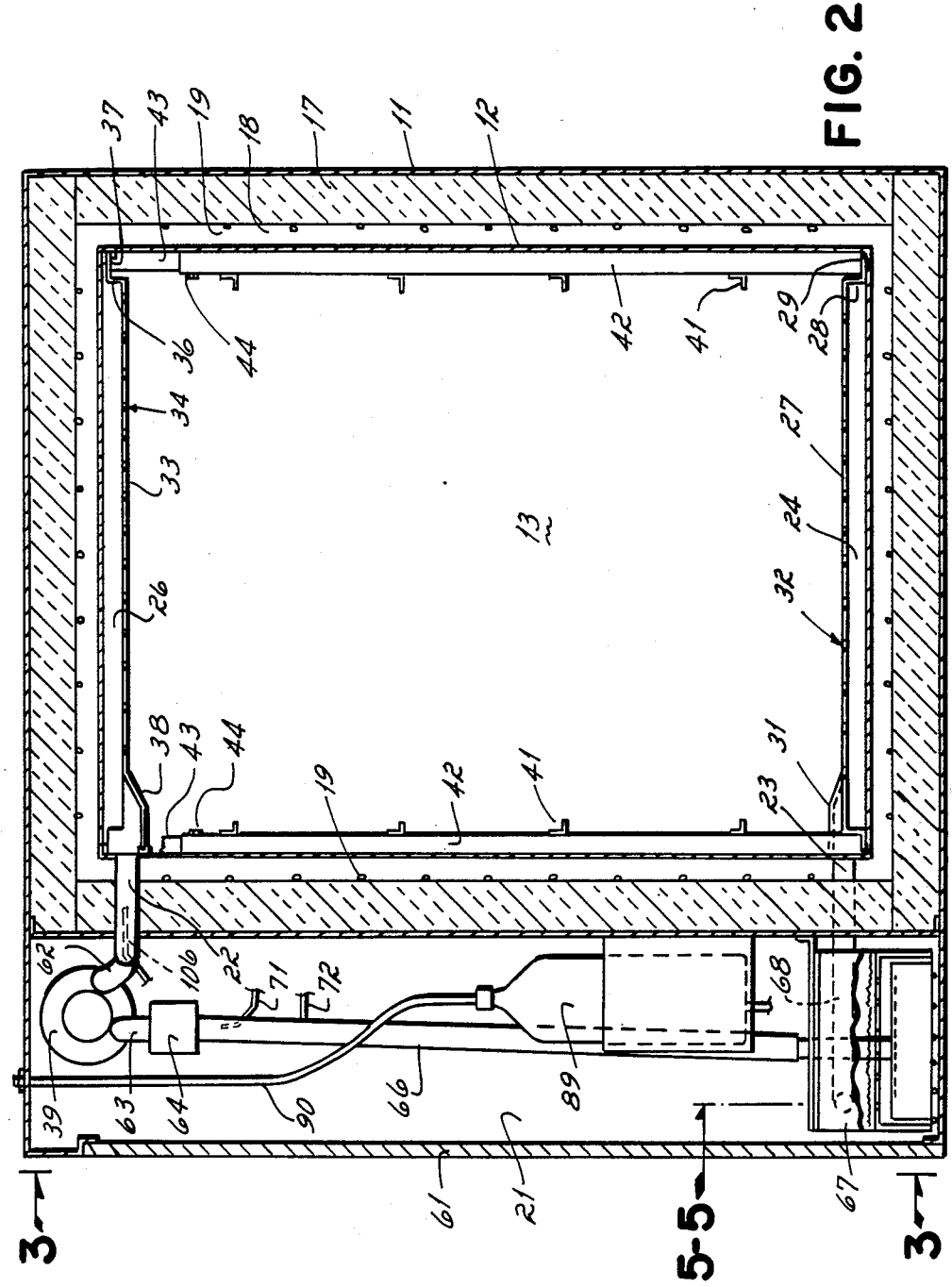
Figure 3:
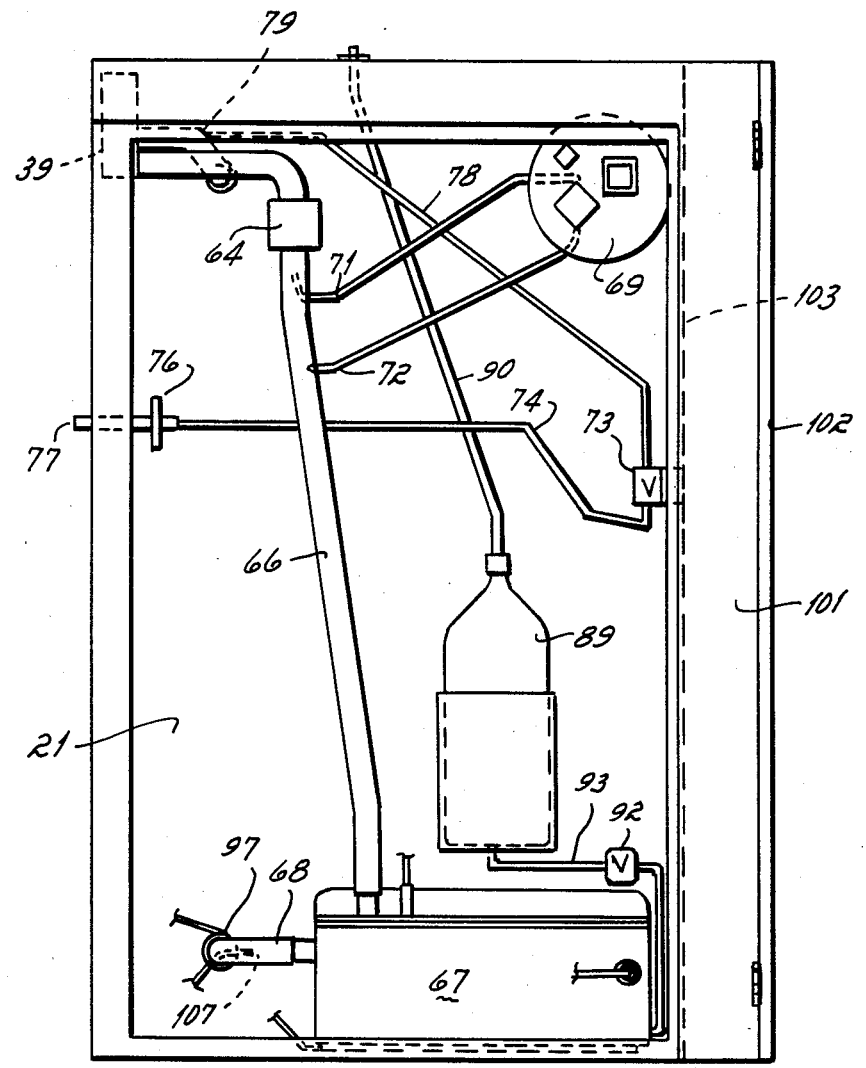
Figure 5:
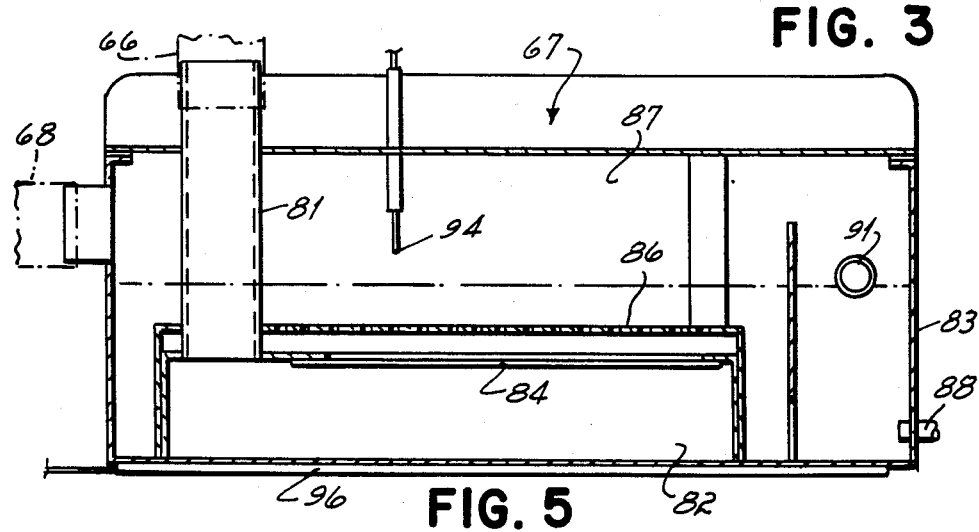
Figure 4:
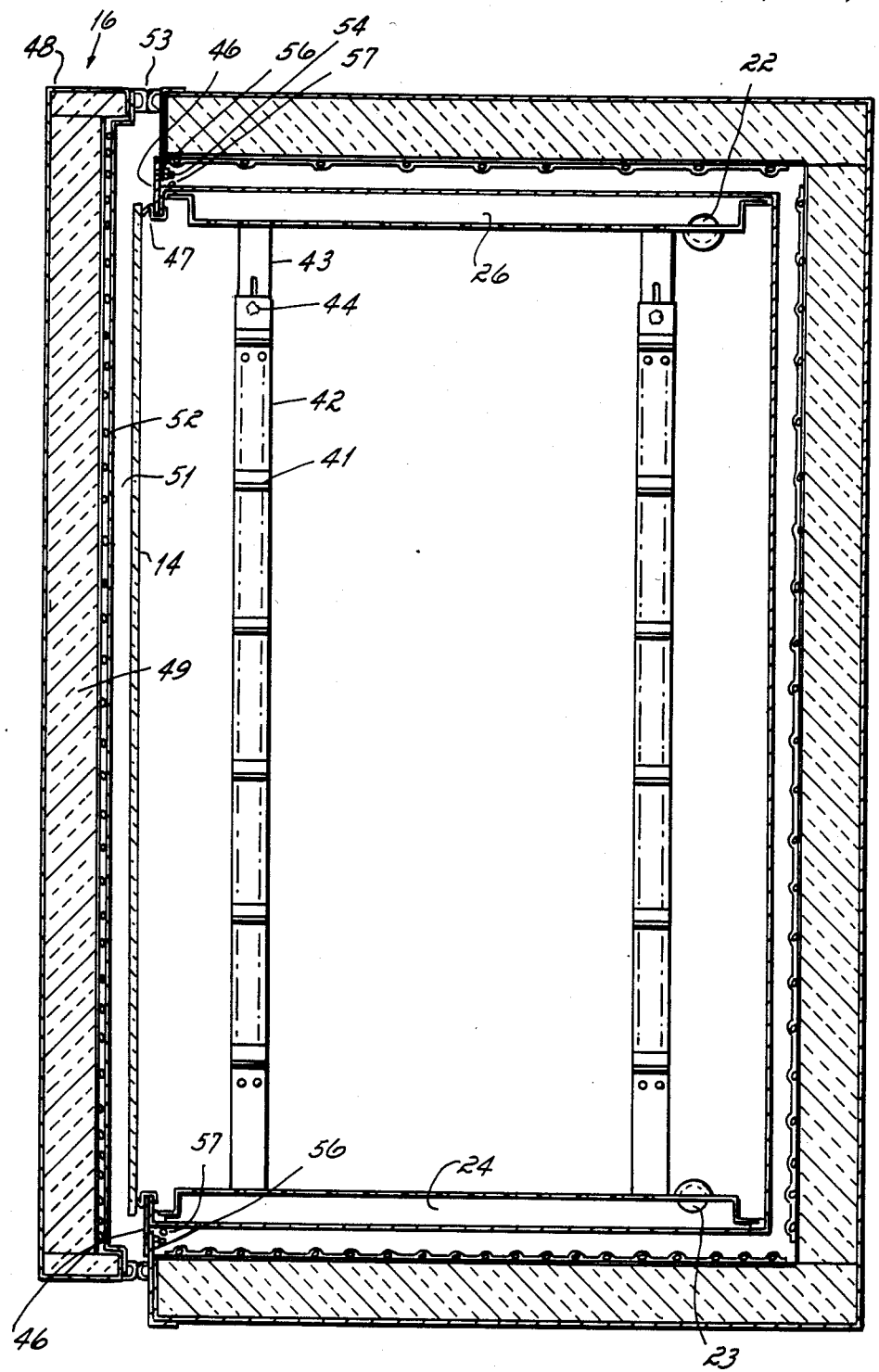
Figure 6:
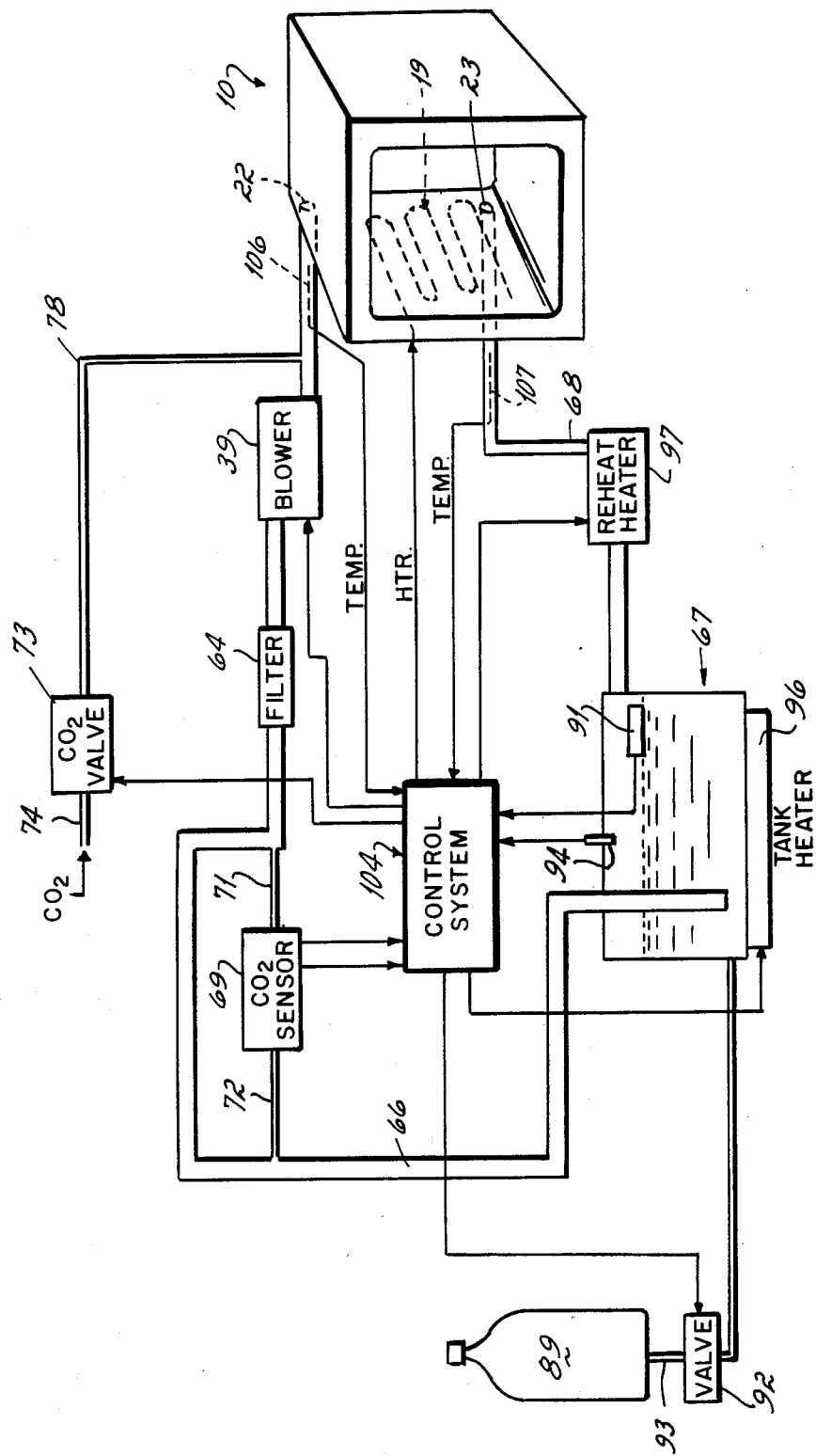
Figure 7:
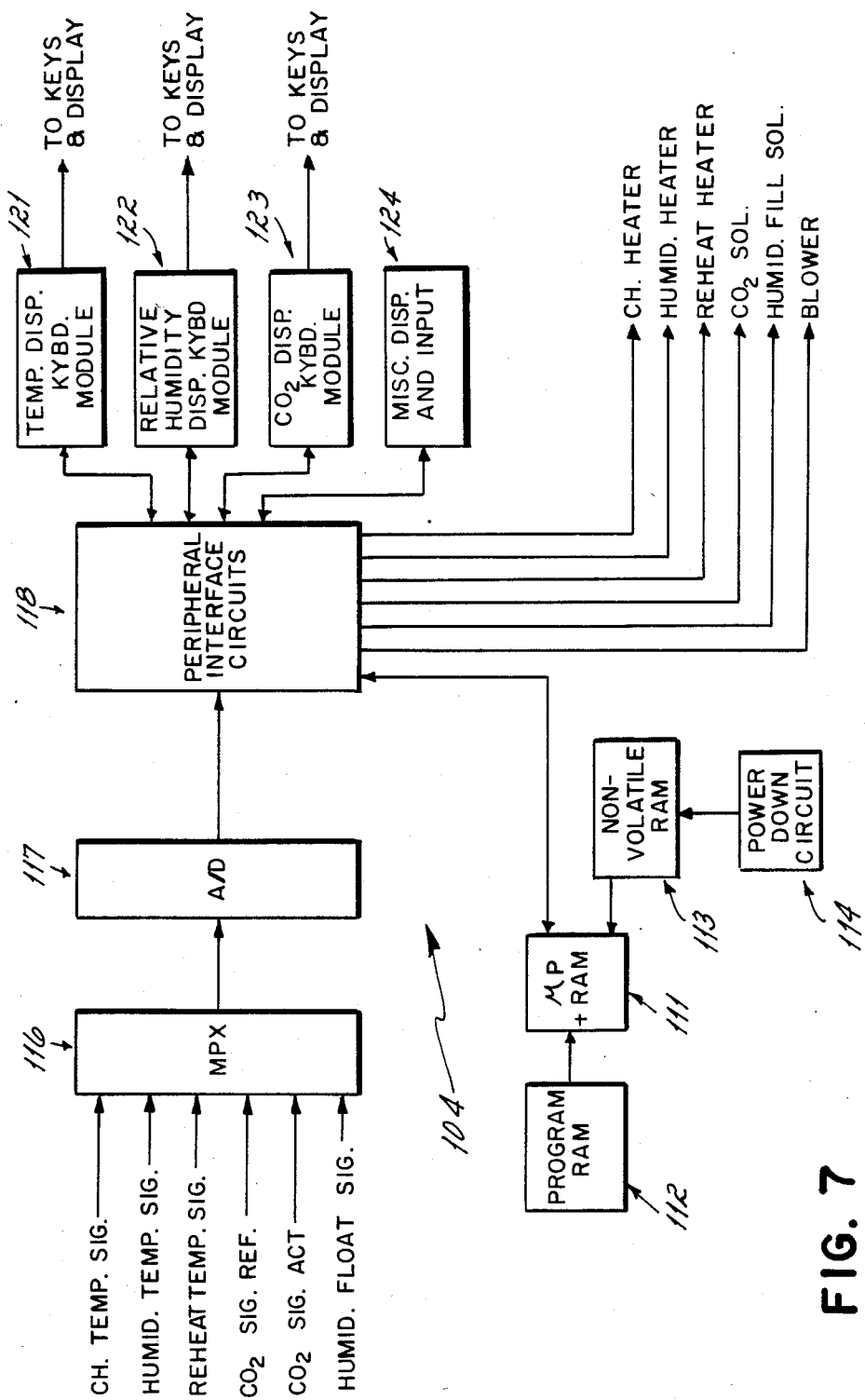

Other advantages of the incubator described herein will become apparent upon reading the following detailed description and upon reference to the drawings, in which:

FIG. 1 is a perspective view of the incubator;
FIG. 2 is a cross sectional view of the incubator of FIG. 1 taken along the line 2—2 of FIG. 1;
FIG. 3 is a cross sectional view of the incubator taken along the line 3—3 of FIG. 2;
FIG. 4 is a cross sectional view of the incubator of FIG. 1 (with its doors closed) taken along the line 4—4 of FIG. 1;
FIG. 5 is a cross sectional view of the humidifier of the incubator, taken along the line 5—5 of FIG. 2;
FIG. 6 is a diagrammatic illustration of various elements of the incubator shown in conjunction with a control system for the incubator;
FIG. 7 is a block diagram illustrating, in further detail, the control system of FIG. 6; and
FIGS. 8–13 are illustrative flow charts of the operation of the microprocessor-based control system of FIGS. 6 and 7.

While the present invention is susceptible to various modifications and alternative forms, a specific embodiment thereof has been shown by way of example in the drawings and will herein be described in detail. It should be understood, however, that it is not intended to limit the invention to the particular form disclosed, but, on the contrary, the intention is to cover all modifications, equivalents, and alternatives falling within the spirit and scope of the invention as defined by the appended claims.

Referring now to the figures, particularly FIG. 1–4, a controlled gas atmosphere incubator 10 constructed in accordance with the present invention includes an outer housing made up of outer walls 11 and inner walls 12 defining a controlled atmosphere incubator chamber 13. The incubator chamber 13 is generally cubical and is bounded on five sides by the walls 12. The outer incubator chamber housing has a corresponding five outer walls 11. The sixth side of the chamber 13, and of the incubator housing, is formed by an inner, transparent door 14, and by an outer door 16, respectively.

The inside surface of the housing walls 11 are covered with a layer of a modified urethane insulation 17 having a relatively high R value, and the chamber walls 12 are spaced inwardly from the insulation 17 to define a substantially closed air space 18 about the chamber. In the air space 18, adjacent the insulation 17 and spaced apart from the chamber walls 12, are electric heating elements 19 for heating the air in the air space 18. In practice, the heating elements 19 are arranged in a serpentine fashion to form a separate heating element array for each of the chamber walls.

In order to condition and circulate the atmosphere of the incubator chamber 13, the incubator 10 includes a gas recirculation path in a control chamber 21 outside the insulated left side wall 11 of the incubator chamber housing. As shall be described, humidity control and $CO_2$ measurement and control are effected in the recirculation path outside the chamber 13. The gas atmosphere of the chamber is drawn into the recirculation path through a chamber outlet 22 and returned through a chamber inlet 23.

An upward vertical laminar flow of the gas atmosphere in the chamber 13 is produced by the provision of a lower plenum 24 communicating with the chamber inlet 23 and an upper plenum 26 communicating with the chamber outlet 22. The lower plenum 24 is defined by a diffuser plate 27 spanning a lower portion of the chamber 13. For the most part, the diffuser plate 27 is spaced apart from the bottom wall of the chamber and has a peripheral vertical side wall 28 terminating in a gasketed flange held in sealing engagement with the bottom wall of the chamber 13 to enclose the plenum 24. The chamber inlet 23 is coupled to an inlet pipe 31, which is structurally a part of the diffuser plate 27, which channels the recirculated gas atmosphere into the lower plenum 24.

The diffuser plate 27 contains an array of apertures 32 through which the recirculated chamber gas atmosphere in the plenum 24 is returned to the chamber 13. The gas atmosphere of the chamber exiting the diffuser plate 27 moves upwardly in a laminar flow pattern to a diffuser plate 33 in the upper portion of the chamber 13, which defines the upper plenum 26. The upper diffuser plate 33 contains an array of apertures 34 through which the gas atmosphere passes into the upper plenum 26. The upper diffuser plate 33 includes a vertical wall 36 about its periphery which terminates in a gasketed peripheral flange 37 maintained in sealing engagement with the top wall of the chamber 13. The upper plenum 26 communicates with the chamber outlet 22 through a pipe 38, which is structurally a portion of the diffuser plate 33. The chamber atmosphere entering the plenum 26 is drawn through the pipe 38 and the chamber outlet 22 into the recirculation path by a blower 39, as shall be described in more detail hereinafter.

In the use of the incubator 10, biological cultures are placed on shelves (not shown) supported by shelf brackets 41 in the incubator chamber 13. The shelf brackets 41 are in turn supported on four pilasters 42, which are removably mounted within the chamber 13. The pilasters 42 further serve the purpose of maintaining the peripheral flanges 29, 37 of the diffuser plates 27, 33 in sealing engagement with the lower and upper walls, respectively, of the chamber. To do this, each pilaster 42 includes a telescoping section 43 which is extendible to enable the pilaster to exert a sealing force upon the flanges 29, 37. Once properly extended, the pilaster section 43 is locked in place by a fastener 44.

Shelves to be employed in the incubator chamber 13 preferably permit the relatively free flow of the chamber atmosphere from the lower diffuser 27 to the upper diffuser 33. In the present incubator, the array of apertures 32 in the diffuser plate 27 is selected to provide a substantially uniform flow rate across a horizontal plane at the level of the lowermost shelf in the incubator chamber. In one incubator construction, the apertures 32 were evenly spaced over the surface of the diffuser plate 27 and contained a total area approximately four times the area of the chamber inlet 23, which had a diameter of one inch.

For a flow rate of about 1,000 feet per minute at a one inch diameter inlet 23, and a flow rate of about 250 feet per minute through the apertures 32, the initial Reynolds number of the laminar flow produced at the first shelf level, two inches above the diffuser plate, was about 30. Since there will be laminar flow in conditions in which the Reynolds number is below about 2,000, flow interference from biological culture containers on the incubator shelves is generally insufficient to disrupt the vertical laminar flow produced by the diffuser 27.

The upper diffuser 33 serves to maintain the laminar flow path of the gas atmosphere through the chamber. In the above-mentioned particular incubator construction, the diffuser plate 33 contained an array of apertures 34 of the same pattern and size as the apertures 32 in the lower diffuser plate 27.

As earlier described, the sixth wall of the interior chamber 13 is formed by a transparent inner glass door 14. A front flange 46 about the inner door opening carries a silicon gasket 47 which seals the periphery of the door 14 to the chamber when the door is closed. In this way, the interior of the incubator chamber 13 may be observed through the transparent door 14 without disturbing the chamber atmosphere.

The inner door 14, forming the sixth wall of the incubator chamber 13, is thermally insulated from the incubator environment by the outer door 16, when the outer door is closed. The outer door 16 includes a metal wall 48 forming a door panel which contains a layer of insulation 49 of the same type as the incubator wall insulation 17. The interior surface of the insulation 49 is spaced apart from the inner door 14 to define an air space 51 therebetween. The air space 51 is heated by a serpentine array of heating elements 52 spaced apart from the inner door 14 and mounted on the interior of the insulation 49. When the door 16 is closed, a magnetic gasket 53 about the periphery of the door engages the incubator housing about the door opening to seal the air space 51.

As thus far described, the heating of the incubator chamber is effected by six serpentine heating element arrays, one associated with each of the six sides of the incubator chamber. One additional heating loop is provided to heat the chamber walls 12 around the door opening. As best shown in FIG. 4, the incubator chamber 13 is mounted in the incubator housing by a series of fasteners 54 securing the front chamber flange 46 to a housing wall flange 46 about the perimeter of the door opening. Due to thermal conductivity between the chamber walls and the housing in this area, there is considerable heat loss from the incubator chamber about the face of the door opening. In order to maintain the chamber temperature at this location, and to thereby prevent condensation around the front of the chamber and the edges of the inner door 14, a heating element loop 57 is positioned at the front of the chamber walls around the door opening.

While the heating elements for the walls and the door of the incubator 10 are shown diagrammatically as being in a more or less evenly distributed array, these heating elements are preferably provided in serpentine arrays in which the spacings and/or wattages of different portions of the array are varied in order to vary the amount of heat produced in different parts of the wall. The purpose in varying the heat density of different parts of the heater arrays is to accomplish uniform temperature distribution, by convection, within the heated air spaces of the chamber walls and the door. In one incubator construction, a heating element array was employed in the bottom wall having a heat density, or watt density, of about twice that of the heating element array employed in the top wall. The watt densities of the side and rear heating element arrays generally decreased from bottom to top, with the watt density at the bottom of each of these arrays being about $\frac{2}{3}$ that of the bottom heater array. The door heater had a higher watt density than the side and rear wall heaters. The top, bottom and side heating element arrays, adjacent the door opening, had significantly greater watt densities in the immediate vicinity of the opening, an increase by about a factor of 10, in order to offset heat losses at the opening. Likewise, a significantly higher watt density was required for the portion of the door heating element array about the periphery of the door.

The particular configurations for the heating element arrays to be utilized depend upon a number of design considerations including heat loss at the door opening, efficiency of insulation, size of air space, size of the chamber, etc. The basic design consideration is the apportionment of the heating capacity of the heating elements to produce a greater amount of heat in the lower portions of the chamber-surrounding air space, and a lesser amount of heat in the upper portions of that air space, so that natural convection within the air space will equalize the temperature of the air around the incubator chamber, and thus the temperature of the chamber itself. In this way, there is no need for a blower or fan to circulate the air in the air space to obtain a uniform chamber temperature.

In order to properly condition the atmosphere of the incubator chamber 13, such as to control $CO_2$ concentration and relative humidity, the atmosphere is recirculated continuously via the upper plenum 26 from the chamber outlet 22 through a recirculation path, returning through the chamber inlet 23 and the lower plenum 24 to the chamber. In the illustrated incubator, the recirculation path is contained within the control chamber 21, accessible by the removal of an end panel 61 from the chamber. In the recirculation path, the chamber gas atmosphere is drawn through a conduit 62 by a centrifugal blower 39 and coupled from the blower outlet through a conduit 63 to a HEPA filter 64. The recirculated, filtered gas is coupled from the filter 64 through a hose 66 to a humidifier 67. The recirculated, humidified, gas exits the humidifier 67 and is coupled through a conduit 68 to the chamber inlet 23 for passage upwardly through the chamber 13.

In order to control the $CO_2$ concentration in the chamber atmosphere, a $CO_2$ sensor 69 receives a sample of the recirculating gas through a sampling loop made up of an inlet tube 71, the sensor 69, and an outlet tube 72. A portion of the recirculating gas is routed through the sensing loop, and the $CO_2$ sensor 69 produces an electrical signal indicative of the $CO_2$ concentration in the recirculating gas.

As shall be described in more detail hereinafter, an electronic control system responds to the measured $CO_2$ concentration, as required, to maintain a selected $CO_2$ level in the recirculating gas. To do this, a $CO_2$ valve 73 is operated by the control system to add $CO_2$ to the recirculating gas when necessary. The valve 73 is connected in series with a $CO_2$ line 74, which is in turn connected through a $CO_2$ filter 76 to an externally accessible $CO_2$ inlet 77 connected to a source of $CO_2$. The $CO_2$ coupled through the valve 73 is connected through a $CO_2$ line 78 to an inlet 79 in the conduit 62 immediately downstream from the chamber outlet 22.

The $CO_2$ sensor 69 is located outside the incubator atmosphere and hence is not subject to the detrimental effects of the incubator chamber humidity or that of any constituent gases in the incubator chamber atmosphere. Also, since the sampling loop for the $CO_2$ sensor 69 is connected to the recirculation path in the hose 66, downstream from the filter 64, a build-up of impurities in the $CO_2$ sensor is substantially avoided. In the illustrated incubator, the $CO_2$ sensor is a non-destructive infrared analyzer such as is sold by Sensors, Inc. of Ann Arbor, Mich.

Although not illustrated in the figures, it is contemplated that additional sensors for other constituent gases in the chamber atmosphere may be added in the sampling loop containing the $CO_2$ sensor. For example, an oxygen sensor in the sampling loop would provide a signal indicative of oxygen concentration in the recirculating gas to the control system, which would in turn control the addition of either oxygen or nitrogen into the recirculating gas as required to maintain a selected oxygen concentration.

The relative humidity of the chamber atmosphere is controlled in the recirculation path by the humidifier 67. As best seen in FIG. 5, the recirculating gas enters the humidifier 67 from the hose 66, passing through a pipe 81 into a compartment 82 below the surface of a quantity of water maintained in a tank 83 of the humidifier. The incoming gas is constrained to exit the compartment 82 through a screen 84 which divides the gas into small bubbles. The gas bubbles pass through openings in a top plate 86 of the compartment 82 to reform as a body of moisture-saturated gas in an area 87 in the upper portion of the humidifier 67. The now-saturated, recirculating gas exits the humidifier through an outlet into the conduit 68 to be returned to the humidifier chamber 13.

Water is replenished in the humidifier tank 83 through a fill line 88 coupled to a water supply bottle 89 in the control chamber 21. The supply bottle may in turn be replenished through a fill tube 90. The need for the addition of water to the tank 83 is indicated by an electrical signal coupled to the incubator control system from a float level sensor 91 in the tank 83. The control system is responsive to a low water level signal from the float 91 to open a valve 92 (FIG. 3) in a water supply line 93 connecting the bottom of the bottle 89 to the humidifier fill inlet 88.

The relative humidity of the chamber atmosphere is controlled by controlling the temperature of the water in the tank 83 of the humidifier 67. The recirculating gas passing through the water in the humidifier is fully saturated and also cooled to the temperature of the water in the humidifier, which is maintained at a temperature below that of the chamber atmosphere. Since the recirculating gas exiting the humidifier 67 is fully saturated, at about the temperature of the water, the measured temperature of the gas above the water corresponds to the dew point temperature of the recirculating, humidified gas. This water temperature is measured by a temperature probe 94 in the tank 83. The temperature probe signal, indicative of the water temperature, is coupled to the incubator control system. The dew point temperature of the humidified, recirculating gas is compared by the control system with the chamber atmosphere temperature to determine the relative humidity of the incubator chamber atmosphere. The control system in turn regulates a humidifier water heater 96 to establish the proper humidifier water temperature to obtain a selected relative humidity of the chamber atmosphere.

In order to enhance temperature uniformity throughout the incubator chamber 13, the recirculating gas exiting the humidifier is reheated by a heating element 97 before reentering the chamber 13 through the chamber inlet 23. The "reheat" heater 97 is controlled by the incubator controller to heat the recirculating gas to the setpoint temperature of the chamber atmosphere.

The incubator control system electronics are contained on a number of circuit boards (not shown) in a forward section 101 of the control chamber 21. The control circuitry is accessible through a door 102, which carries a number of display and keyboard modules mounted thereon and which are accessible to the user from the exterior of the incubator housing. The forward portion 101 of the control chamber 21 is separated from the rear portion of the control chamber by a vertical metal shield 103.

With reference now to FIG. 6, the incubator control system, indicated generally 104, is a microprocessor-based control system coupled to the sensors, loads and heaters of the incubator 10. The control system 104 controls the activation of all of the arrays of heating elements 19 to maintain the incubator chamber 13 at a selected temperature. In the illustrated incubator, all of the chamber heating element arrays, including the door heater and the loop 54, are simultaneously either actuated or deactuated as a group. In order to operate the heaters to maintain the selected chamber temperature, the control system 104 is coupled to a temperature sensor 106 immediately downstream from the chamber outlet 22 in the conduit 62. The control system 104 controls the chamber heating elements to maintain the selected temperature as sensed by the temperature probe 106.

The control system 104 also controls the operation of the blower 39. The blower 39 operates substantially continuously, but is deactivated by the control system 104 when the inner incubator door 14 is opened, as indicated by a door ajar sensor (not shown).

The control system 104 also receives a reference $CO_2$ signal and an actual $CO_2$ signal from the $CO_2$ sensor 69. In response to the $CO_2$ concentration indicated in the recirculating gas by the sensor signals, the control system 104 activates the $CO_2$ valve 73 as required to add $CO_2$ to the recirculation path in order to maintain the selected $CO_2$ concentration in the chamber atmosphere.

The control system 104 also interacts with the various components of the humidifier 67. The float level sensor 91 is coupled to the control system 104 to indicate a low water level in the humidifier tank, and the control system controls the water valve 92 to couple water from the water bottle 89 to the tank as necessary in response to float level sensor signals. The control system 104 is also coupled to the reheat heater 97 to reheat the cooled, humidified gas exiting the humidifier to the setpoint temperature of the incubator chamber atmosphere. The temperature of the reheated recirculating gas is measured by a temperature probe 107, which provides a temperature signal to the control system 104. The control system 104 activates the reheat heater 97 in order to maintain the temperature at the probe 107 equal to the setpoint temperature.

The control system 104 is also operable to establish the desired relative humidity for the gas atmosphere of the incubator chamber 13. In order to do this, the control system 104 receives a temperature signal from the temperature probe 94, which is in the area 87 of the humidifier tank. The control system 104 is also coupled to the humidifier tank heater 96 and actuates the heater to maintain the water in the humidifier tank at a certain temperature. Since the temperature of the water in the humidifier tank corresponds to the dew point temperature of the recirculating gas exiting from the humidifier, the control system can establish the relative humidity of the gas atmosphere in the incubator chamber by maintaining the requisite temperature differential between the dew point temperature of the humidified, recirculating gas and the chamber temperature, as measured by the temperature sensors 94 and 106, respectively. There is a calculable relationship between the dew point temperature of a gas and the relative humidity of that same gas at a temperature higher than the dew point temperature. This relationship may be calculated by the control system, or the control system may include a table stored in memory for the values of this relationship over a range of temperature differentials of interest.

Considering the control system 104 in more detail, and with reference to FIG. 7, the control system includes a microprocessor, with associated random access memory (RAM), 111 and a program read only memory (ROM) 112 coupled to the microprocessor 111. The control system also includes a non-volatile RAM 113 for retaining previously selected setpoints and initial conditions when the incubator is turned off. The non-volatile RAM 113 is controlled by a power down circuit 114 to assure the storage of accurate data when the incubator is turned off. In the present system, the microprocessor is a Motorola 6802 processor, having an associated RAM memory.

The various input signals which are coupled to the control system 104, as illustrated in FIG. 6, are coupled through a multiplex circuit 116 and an analog-to-digital converter circuit 117 to peripheral interface circuitry 118. The microprocessor 111 regularly receives input data from each of the signal inputs, in sequence, on an interrupt basis. The microprocessor 111 also activates the various heater and solenoid valve loads, and the blower 39, on output lines coupled from peripheral interface circuits 118.

The microprocessor 111 further communicates through the peripheral interface circuitry 118 with a temperature display and keyboard module 121, a relative humidity display and keyboard module 122, a $CO_2$ display and keyboard module 123, and other miscellaneous displays and inputs 124. The modules 121, 122 and 123 each contain an LCD display operable to show either the value of the actual parameter or the value of the setpoint parameter. Each module also includes a set of three pushbuttons, one of which is operable to determine whether the actual or setpoint parameter is to be displayed. The other two pushbuttons are operable to change the setpoint parameter to a larger or smaller value.

Other displays and inputs include, for example, a door ajar light, a pilot light, and an on/off switch. In a case in which an oxygen sensor is provided in the sensing loop, as earlier discussed, an oxygen display and keyboard module is provided.

Figures 8, 9:
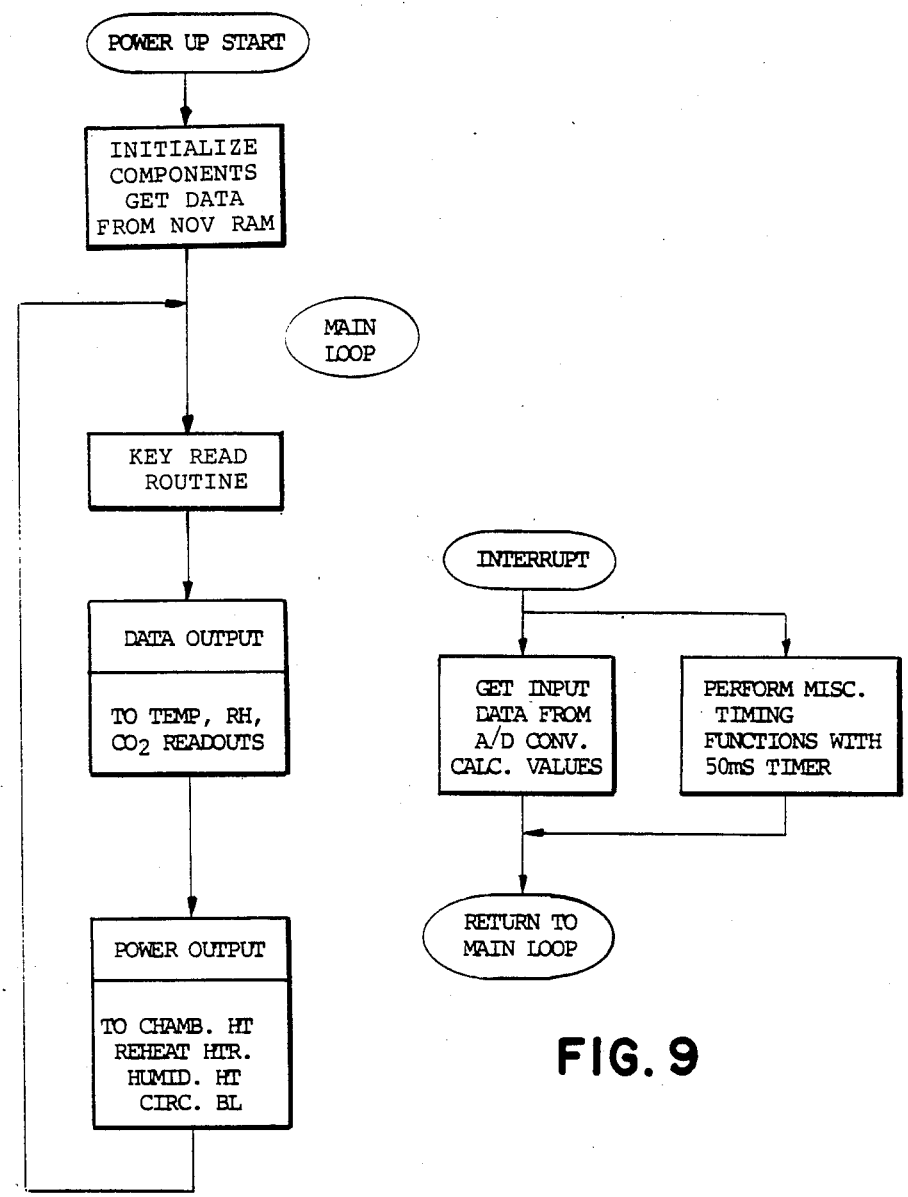

The microprocessor 111 cooperates with its associated RAM memory and the program ROM 112 and non-volatile RAM 113 to continuously execute a main program loop, which is entered after a power up start routine, when the incubator is first turned on. The main program loop is also interrupted to permit the processor to perform two interrupt routines. As shown generally in FIG. 8, after the incubator is turned on, the microprocessor performs a power up start routine in which the peripheral interface circuitry is initialized and data is read from the non-volatile RAM. The processor then continuously loops through the main program loop, reading keys, updating the displays, and driving the output devices such as the heaters and solenoids. During the execution of the main program loop, the microprocessor is periodically interrupted, as generally shown in FIG. 9, to perform one of two interrupt routines. As each data input is converted by the A/D converter 117 via the multiplexer 116, the processor is interrupted to read the input data from the analog to digital converter and calculates any necessary values based upon the just-read data. On a timed interrupt basis, the processor also performs miscellaneous timing functions using a 50 millisecond timer routine. These two interrupt routines are illustrated in general terms in FIG. 9.

Figure 10:
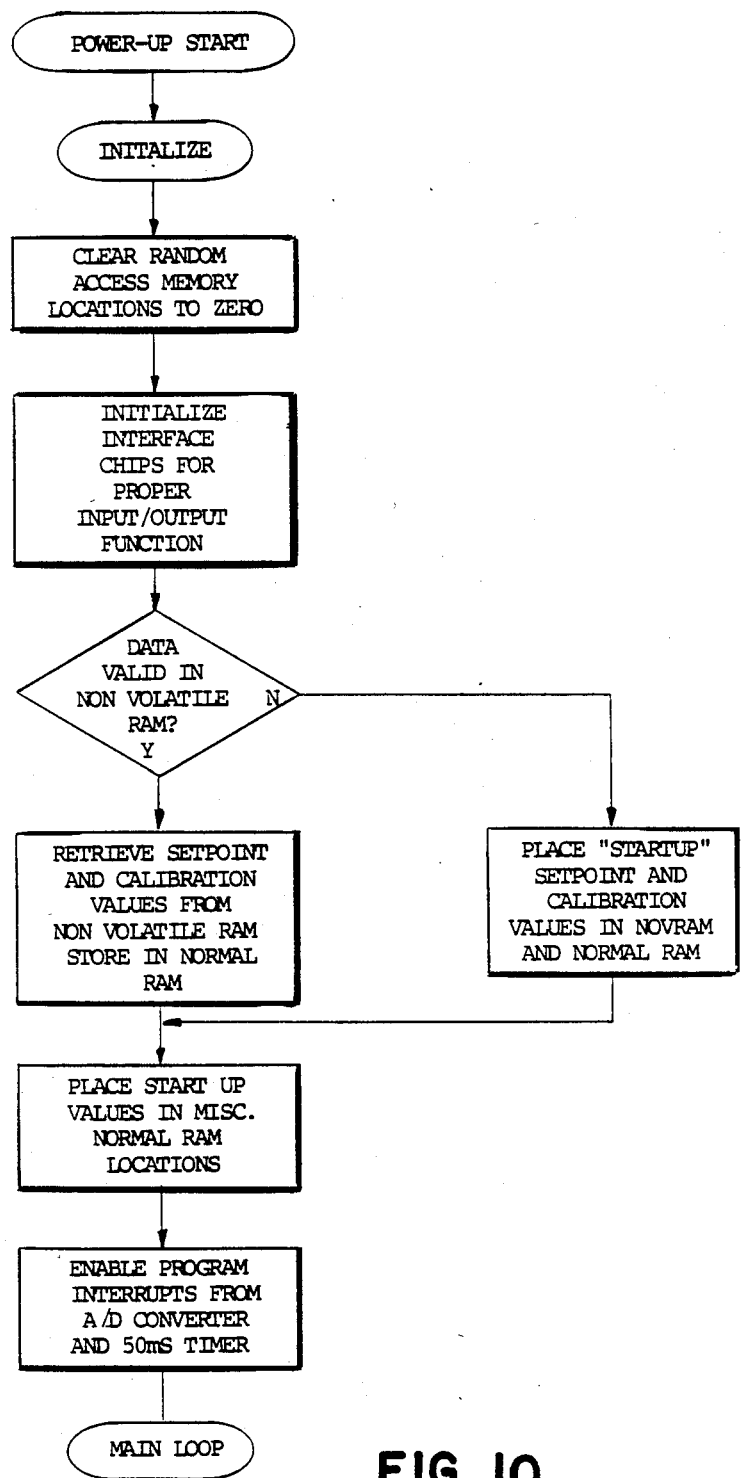

The power up start routine of FIG. 8 is shown in further detail in FIG. 10. In this routine, the processor initializes conditions by clearing the RAM memory locations and initializing the interface circuitry for proper input/output functions. If there is no valid data in the non-volatile RAM, the processor places start up setpoint and calibration values in the non-volatile RAM and its RAM. If there is valid data in the non-volatile RAM, the processor retrieves setpoint and calibration values from the non-volatile RAM for storage in RAM. Start up values for the various functions to be controlled by the processor are placed in the appropriate RAM locations, and the program interrupts from the analog to digital converter and the 50 millisecond timer are now enabled as the processor enters the main program loop.

Figure 11A:
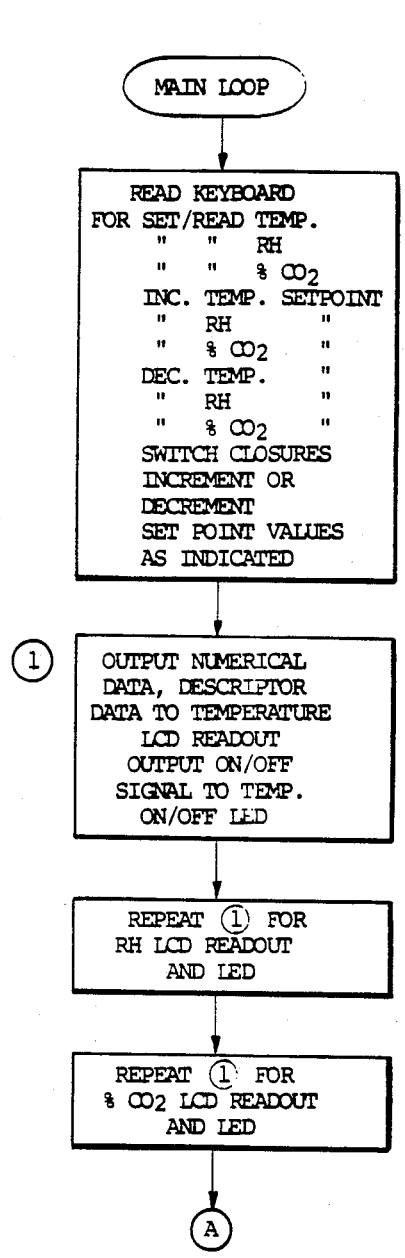
Figure 11B:
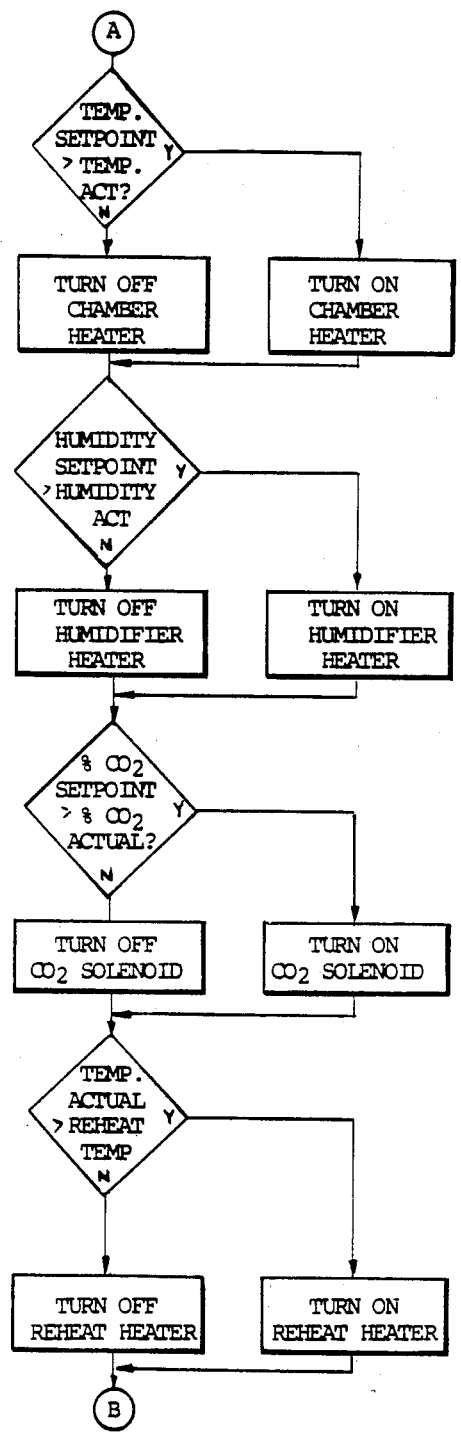
Figure 11C:
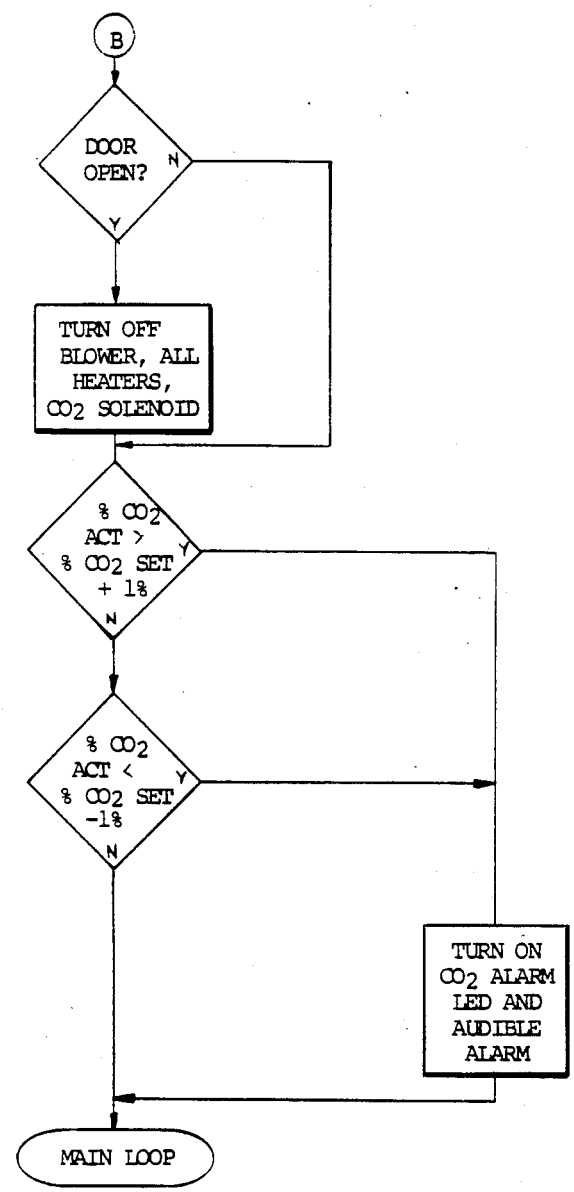

The main program loop is shown in further detail in FIGS. 11a, 11b and 11c. In executing the loop, the processor first checks the status of the set/read keys, or pushbuttons, for the temperature, relative humidity, and $CO_2$ modules. The condition at each of these keys determines whether the parameter to be displayed for that module is the setpoint parameter or the actual parameter. The processor then effects any requested incrementing or decrementing of setpoint parameters. Next, the processor outputs the selected setpoint or actual temperature to the LCD display of the temperature module. If the chamber heater element arrays are energized, an LED on the module is also activated. The processor performs similar functions for the relative humidity and $CO_2$ modules.

The processor then activates or deactivates the chamber heating element arrays, dependent upon the relative values of the chamber setpoint temperature and the actual chamber temperature. In a preferred form of control system, the chamber heating elements are activated on a proportional control basis.

Similarly, the processor produces control signals for the humidifier heater, $CO_2$ solenoid, and reheat heater, dependent upon the sensed actual conditions. The processor then checks to determine if the outer door is open, and if the door is open the processor turns off the blower, heaters, and $CO_2$ solenoid valve. Finally, the processor determines if the $CO_2$ concentration has deviated from the setpoint by more than 1% and turns on a $CO_2$ alarm LED and an audible alarm if this has occurred.

Figures 12, 13:
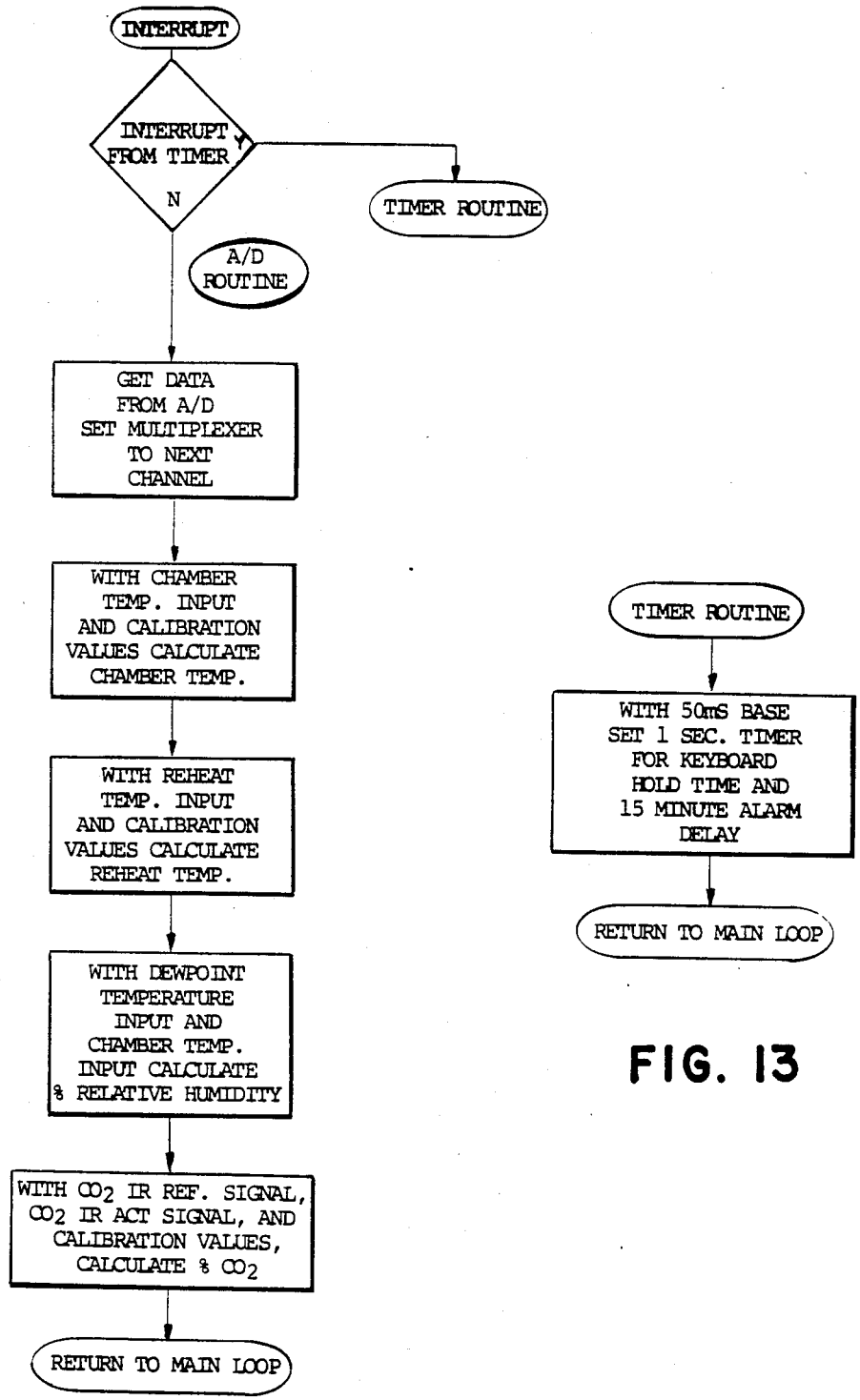

The interrupt routines are illustrated in further detail in FIGS. 12 and 13. When the processor is interrupted, it first determines if the interrupt is from the 50 millisecond timer, and if it is not, the processor proceeds with the analog to digital interrupt routine.

In the analog to digital routine, the processor reads the data from the analog to digital converter circuit and increments the multiplexer to the next data channel. For a chamber temperature input, the processor utilizes the stored calibration values and calculates the actual chamber temperature. For a reheat heater temperature input, the processor utilizes the stored calibration values to calculate a reheat temperature. For a humidifier (dew point) temperature input, and also in the case of a chamber temperature input, the processor calculates a percentage of relative humidity based upon the difference in these temperatures. For a $CO_2$ reference signal or a $CO_2$ actual signal, the processor utilizes these two values, and appropriate calibration values, to calculate the $CO_2$ concentration. The processor then returns to the main loop.

If the interrupt has occurred from the 50 millisecond timer, the processor enters the timer interrupt routine of FIG. 13. The processor uses these known timed interrupts to determine if a key for incrementing or decrementing a setpoint parameter has been depressed for one second, in order to begin rapidly incrementing or decrementing the setpoint. This facilitates changing the setpoint in that repeated depressions of the increase or decrease setpoint buttons are not required. In the timer routine, the processor also maintains a 15 minute alarm delay timer, at which time an alarm condition which has been reset will again be annunciated. After the execution of the timer interrupt routine, the processor returns to the main loop.

What is claimed is:

1. A warm air jacket controlled atmosphere incubator comprising:
    a housing having (a) inner walls, each having an outer surface, defining a controlled atmosphere chamber and (b) insulated outer walls, each having an inner surface, spaced apart from the inner walls, with the outer surface of each inner wall cooperating with the inner surface of an outer wall to define an air space therebetween, all of said air spaces being interconnected;
    a plurality of individual heating element arrays, a different one of said arrays being mounted adjacent the inner surface of each outer wall of the housing so that there is an individual heating element array spaced apart from the outer surface of an inner wall in each of the air spaces, the heating element arrays having greater heat densities near lower portions of the controlled atmosphere chamber than near upper portions of the controlled atmosphere chamber and the interconnected air spaces being isolated from the controlled atmosphere chamber;
    means for measuring the temperature of the chamber atmosphere; and
    means, coupled to the temperature measuring means, for controlling the energization of the heating element arrays to maintain a selected temperature in the chamber, air in the air spaces moving by convection to tend to equalize the temperature in the air spaces, due in part to the heat density differences in the heating element arrays, whereby the chamber temperature is equalized.

2. The incubator of claim 1 in which the housing includes an inner door forming an inner wall of the chamber and an insulated outer door, forming an outer wall, spaced apart from the inner door to define an air space therebetween, and further comprising a heating element array in said door air space, spaced apart from the inner door.

3. The incubator of claim 2 in which the heating element array in the door air space has a greater heat density in the air space adjacent the lower portion of the door than adjacent an upper portion of the door.

4. The incubator of claim 3 which further comprises, in the chamber air space adjacent said doors, a heating element loop in thermal contact with the inner walls adjacent the doors.

* * * * *